United States Patent
Russmann et al.

(10) Patent No.: US 8,956,344 B2
(45) Date of Patent: Feb. 17, 2015

(54) APPARATUS AND METHOD FOR GENERATING CUT SURFACES IN THE CORNEA OF AN EYE FOR CORRECTION OF AMETROPIA

(75) Inventors: Christoph Russmann, Jena (DE); Juergen Kuehnert, Jena (DE); Wilfried Bissmann, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 2004 days.

(21) Appl. No.: 12/109,917

(22) Filed: Apr. 25, 2008

(65) Prior Publication Data

US 2008/0275433 A1    Nov. 6, 2008

Related U.S. Application Data

(60) Provisional application No. 60/914,177, filed on Apr. 26, 2007.

(30) Foreign Application Priority Data

Apr. 26, 2007   (DE) .................. 10 2007 019 813

(51) Int. Cl.
  *A61F 9/01*   (2006.01)
  *A61F 9/008*  (2006.01)
(52) U.S. Cl.
  CPC ............. *A61F 9/008* (2013.01); *A61F 9/00827* (2013.01); *A61F 9/00829* (2013.01); *A61F 9/00838* (2013.01); *A61F 2009/00872* (2013.01); *A61F 2009/00897* (2013.01)
  USPC ............ 606/5; 606/4; 606/6; 606/10; 606/11; 606/27; 604/21; 623/5.11
(58) Field of Classification Search
  USPC .......... 606/4–6, 10–12, 27; 604/21; 623/5.11
  See application file for complete search history.

(56) References Cited

U.S. PATENT DOCUMENTS 5,123,902 A * 6/1992 Muller et al. ................ 604/21
5,620,437 A * 4/1997 Sumiya ........................ 606/5

(Continued)

FOREIGN PATENT DOCUMENTS

| CA | 2 620 095 A1 | 4/2007 |
| DE | 690 33 274 T2 | 4/2000 |

(Continued)

OTHER PUBLICATIONS

Lubatschowski H., et al., "Application of ultrashort laser pulses for intrastromal refractive surgery," *Graefe's Arch Clin Exp Ophthalmol*, vol. 238, pp. 33-39 (2000).

(Continued)

*Primary Examiner* — William Thomson
*Assistant Examiner* — Victor Shapiro
(74) *Attorney, Agent, or Firm* — Patterson Thuente Pedersen, P.A.

(57) ABSTRACT

An apparatus for generating cut surfaces in the cornea of an eye in order to correct ametropia is provided, said apparatus comprising a laser unit, which can focus pulsed laser radiation into the cornea and move it therein in order to generate cut surfaces, and a control unit, which controls the laser unit for generating cut surfaces such that a predetermined lenticle to be removed is separated from the surrounding corneal material in the cornea by at least one cut surface, and that at least two mutually spaced apart cut surfaces are formed as opening cuts, each extending from the lenticle to the anterior corneal surface, the position and shape of the opening cuts being selected such that the opening cuts contribute to the correction of the ametropia of the eye or do not counteract the correction of the ametropia of the eye.

29 Claims, 4 Drawing Sheets

(56) References Cited

U.S. PATENT DOCUMENTS

| | | | |
|---|---|---|---|
| 5,800,424 A * | 9/1998 | Sumiya | 606/4 |
| 5,891,132 A * | 4/1999 | Hohla | 606/5 |
| 5,919,185 A * | 7/1999 | Peyman | 623/5.11 |
| 5,970,984 A | 10/1999 | Wakil et al. | |
| 5,993,438 A | 11/1999 | Juhasz et al. | |
| 6,110,166 A * | 8/2000 | Juhasz | 606/5 |
| 6,210,399 B1 | 4/2001 | Parel et al. | |
| 6,364,875 B1 * | 4/2002 | Stanley, III | 606/27 |
| 6,730,074 B2 * | 5/2004 | Bille et al. | 606/5 |
| 7,131,968 B2 | 11/2006 | Bendett et al. | |
| 7,351,241 B2 | 4/2008 | Bendett et al. | |
| 8,182,471 B2 * | 5/2012 | Yee | 606/5 |
| 2002/0193704 A1 * | 12/2002 | Goldstein et al. | 600/558 |
| 2003/0014042 A1 * | 1/2003 | Juhasz et al. | 606/5 |
| 2004/0243111 A1 | 12/2004 | Bendett et al. | |
| 2008/0051772 A1 * | 2/2008 | Suckewer et al. | 606/5 |
| 2008/0065052 A1 * | 3/2008 | Bischoff et al. | 606/4 |
| 2008/0319428 A1 * | 12/2008 | Wiechmann et al. | 606/5 |

FOREIGN PATENT DOCUMENTS

| | | |
|---|---|---|
| DE | 10 2005 014 760 A1 | 10/2006 |
| DE | 10 2005 049 281 A1 | 4/2007 |
| EP | 1941849 B1 * | 7/2010 |
| WO | WO 2004/105661 A1 | 12/2004 |

OTHER PUBLICATIONS

Ratkay-Traub I., et al., "First Clinical Results With the Femtosecond Neodynium-glass Laser in Refractive Surgery," *Journal of Refractive Surgery*, vol. 19(2), pp. 94-103 (2003).

Luce D.A., "Determining in vivo biomechanical properties of the cornea with an ocular response analyzer," *J. Cataract Refract Surg*, vol. 31, pp. 156-162 (2005).

Jaycock, P.D., et al., "Interferometric technique to measure biomechanical Changes in the cornea induced by refractive surgery," *J. Cataract Refract Surg*, vol. 31, pp. 175-184 (2005).

Pinsky P.M., "Computational modeling of mechanical anisotropy in the cornea and sclera," *J. Cataract Refract Surg*, vol. 31, pp. 136-145 (2005).

*Intralase Product Leaflet*, Essential Technology for Biomechanical Stability, Intralase Corp., 6 pgs. (2006).

* cited by examiner

APPARATUS AND METHOD FOR GENERATING CUT SURFACES IN THE CORNEA OF AN EYE FOR CORRECTION OF AMETROPIA

CROSS-REFERENCES TO RELATED APPLICATIONS

This application claims priority from German Application No. 10 2007 019 813.4, filed Apr. 26, 2007 and from U.S. Provisional Application No. 60/914,177 filed Apr. 26, 2007, the disclosures of which are hereby incorporated by reference.

BACKGROUND OF THE INVENTION

1. Field of the Invention

The invention relates to an apparatus for generating cut surfaces in the cornea of an eye in order to correct ametropia, said apparatus comprising a laser unit, which can focus pulsed laser radiation for generating cut surfaces into the cornea and move the radiation therein, and a control unit, which controls the laser unit for generating cut surfaces such that a predetermined lenticle to be removed is separated from the surrounding corneal material in the cornea by at least one cut surface and such that at least two mutually spaced apart cut surfaces are formed as opening cuts, each extending from the lenticle to the anterior corneal surface.

The invention further relates to a method for generating cut surfaces in the cornea of an eye in order to correct ametropia, wherein the pulsed laser radiation for generating cut surfaces is focused into the cornea and moved therein such that a predetermined lenticle to be removed is separated from the surrounding corneal material in the cornea by at least one cut surface and such that at least two mutually spaced apart cut surfaces are formed as opening cuts, each extending from the lenticle to the anterior corneal surface.

2. Background

Such apparatus and method are known, for example, from WO 2004/105661 A1. However, the desired correction of ametropia of the eye is frequently not achieved by such apparatus and method.

SUMMARY OF THE INVENTION

In view thereof, it is an object of the invention to improve an apparatus of the above-mentioned type to overcome the described disadvantage. Further, a corresponding method of the invention is improved accordingly.

Said object is achieved by an apparatus of the type mentioned above for generating cut surfaces in the cornea of an eye in order to correct ametropia in that the position and shape of the opening cuts are selected such that the opening cuts contribute to the correction of the ametropia of the eye or do not counteract the correction of the ametropia of the eye.

It has been discovered that the opening cuts themselves, although being very small, may lead to an undesirable deterioration of the eye's ametropia. Since this effect of the opening cuts is now being taken into account for the first time by the apparatus of the invention, this advantageously allows the opening cuts to contribute to the correction of ametropia or not to counteract the correction of the eye's ametropia. The opening cuts according to the invention accomplish the foregoing advantages because they are neutral with respect to the ametropia to be corrected and/or do not cause any additional ametropia. Thus, for example, when correcting myopia or hyperopia, the opening cuts can be prevented from causing an undesired astigmatism.

Thus, the apparatus according to the invention for generating cut surfaces in the cornea of an eye in order to correct ametropia advantageously benefits from the fact that an opening cut, which is to be provided and through which the lenticle can be removed, is also simultaneously taken into account with respect to the correction of the eye's ametropia. It has turned out that favorable results can be achieved by providing two or more opening cuts. Providing two or more opening cuts has the advantage that they can be used, for example, to rinse the area being operated on (cut area of the lenticle).

Further, the inclusion of the opening cuts in the correction of ametropia is advantageous insofar as the lenticle volume to be removed can be minimized. Thus, reductions in thickness from several µm up to 100 µm can be achieved. This allows, for example, minimizing mechanical weakening of the cornea, if such weakening is caused by material removal or lenticle removal, respectively.

The opening cuts are provided such that it is not possible to fold back a corneal lamella as in the known LASIK operation (laser in situ keratomileusis). Thus, the opening cuts do not lead to a flap of the type provided and folded back in the LASIK operation.

The ametropia to be corrected may be, for example, myopia, hyperopia, astigmatism or presbyopia. It is also possible for the present invention to correct higher-order errors of refracting power. In particular, fourth-order errors of refracting power (spherical aberrations) lead to problems with night vision. Thus, these errors of refracting power of the cornea, or ametropias, can also be corrected by the apparatus according to the invention.

The present control unit may control the laser unit to thereby generate at least three mutually spaced apart opening cuts such that the centers of area of the opening cuts coincide with the corners of a regular polygon. In this case, it is possible, for example, that the opening cuts do not cause additional astigmatism.

The geometrical shape may be the same for each opening cut, although it is also possible to select different geometrical shapes. Thus, for example, the control unit may control the laser unit such that the cut length of at least one opening cut from the anterior corneal surface to the lenticle differs from the cut length of the other opening cuts.

Further, the control unit may control the laser unit to generate exactly two mutually spaced apart opening cuts such that the centers of area of the opening cuts are located on a straight line which, when viewed in a top view of the eye, is parallel to one axis of astigmatism of the eye or intersects said axis at a maximum angle of 10°. This enables a correction for astigmatism. Preferably, the steepest axis of astigmatism is selected (i.e., that axis in relation to which the greatest astigmatism is present).

The control unit can control the laser unit such that at least one of the opening cuts, when viewed in a top view of the eye, has the geometrical shape of a circular ring segment. This shape can be realized with particular ease using conventional laser units in ophthalmic correction apparatuses.

In particular, the control unit can control the laser unit such that the opposite straight sides of the circular ring segment enclose an angle of 30°-120°, 45°-80°, or 30°-60°.

Further, the control unit can control the laser unit such that the opposite straight sides of the circular ring segment have a length of 0.1-1 mm or 0.2-0.4 mm, when viewed in a top view.

In the apparatus according to the invention, the control unit can control the laser unit such that a further cut surface is provided as a relieving cut, which extends from the anterior co-meal surface into the cornea, but not up to the lenticle. The location and shape of the relieving cut may be selected so as to contribute to the correction of the eye's ametropia. Of course, several relieving cuts can be provided. Due to the additional relieving cut or cuts, an effective correction of ametropia can be achieved.

The control unit can control the laser unit such that at least one of the cut surfaces is generated as a perforated cut surface. A perforated cut surface is understood herein to be a cut surface which is not entirely continuous, but comprises material bridges which break away under a predetermined mechanical load (for example, by removal of the lenticle).

In a method of the above-mentioned type, the location and shape of the opening cuts are selected such that they contribute to the correction of the eye's ametropia or do not counteract the correction of the eye's ametropia.

Using the method according to the invention, it is therefore possible to provide the required opening cuts such that they contribute to the correction of ametropia or do not counteract the correction of ametropia. This makes it possible to minimize the material volume of the lenticle to be removed. In particular, the lenticle need not be provided, for example, to compensate for imaging errors caused by the opening cuts, which would otherwise disadvantageously lead to a greater material volume to be removed from the cornea.

In the method of this invention, the position and shape of the opening cuts may be selected such that the correction of the ametropia of the eye is not counteracted in such a manner that the opening cuts do not generate additional astigmatism of the eye. This makes it possible to correct myopia or hyperopia in which the patient, while no longer being near-sighted or far-sighted, has an ametropia in the form of an astigmatism.

The ametropia to be corrected may be myopia, hyperopia, astigmatism and/or presbyopia. The ametropia may further comprise higher-order errors of refracting power, as well. In particular, the ametropia may include fourth-order errors of refracting power such as spherical aberration, which plays a major role in night vision capacity.

In the method of this invention, at least three mutually spaced apart opening cuts can be generated such that their centers of area coincide with the corners of a regular polygon. In this case, it is probable that the opening cuts will not cause additional astigmatism.

The cut length of at least one opening cut from the anterior corneal surface to the lenticle may be made to differ from the cut lengths of the other opening cuts. The opening cuts may also have the same or differing geometrical shapes and/or dimensions.

In one method of the invention, exactly two mutually spaced apart opening cuts can be generated such that their centers of area are located on a straight line which, when viewed in a top view of the eye, is parallel to an axis of astigmatism of the eye (preferably the steepest axis of astigmatism) or intersects said axis at a maximum angle of 10°. Such spaced apart opening cuts enable effective correction of astigmatism.

These opening cuts may be executed such that at least one of the opening cuts, when viewed in a top view of the eye, has the geometrical shape of an circular ring segment. Such a shape can be easily realized using a laser unit of a conventional ophthalmic correction apparatus.

In particular, the opening cut may be carried out such that the opposite straight sides of the circular ring segment enclose an angle of 30°-120°, 45°-80°, or 30°-60°.

Further, the at least one opening cut may be carried out such that opposite straight sides of the circular ring segment have a length of 0.1-1 mm or 0.2-0.4 mm.

In one present method, a further cut surface may be formed as a relieving cut, extending from the anterior cornmeal surface into the cornea, but not up to the lenticle. The position and shape of the relieving cut may be selected such that the cut contributes to the correction of the ametropia. One or several mutually spaced apart relieving cuts can be formed, the opening cut(s) enable(s) improving correction of ametropia.

In one present method, at least one of the cut surfaces may be formed as a perforated cut surface, thereby resulting in smoother cut surfaces, as compared to cut surfaces produced as continuous cut surfaces by pulsed laser radiation.

In particular, one method of this invention allows the lenticle separated from the surrounding corneal material to be removed from the cornea through one of the opening cuts.

It is further possible to divide the lenticle into two or more parts by the pulsed laser radiation and to remove said parts of the lenticle from the cornea through one or more opening cuts.

Further, the opening cuts may also be used to effect flushing of the cut surfaces or, where applicable, to introduce drugs.

Further, a method is provided for generating control data for a control unit of a correcting apparatus for generating cut surfaces in the cornea of an eye. The correcting apparatus may comprise a laser unit and a control unit. The laser unit may focus pulsed laser radiation into the cornea in order to generate cut surfaces and move said radiation therein. The control unit for the laser unit generates control data, thereby allowing the control unit to control the laser unit, on the basis of the control data to generate cut surfaces, such that a predetermined lenticle to be removed is separated from the surrounding corneal material in the cornea through at least one cut surface and such that at least two mutually spaced apart cut surfaces are provided as opening cuts. Each opening cut may extend from the lenticle to the anterior corneal surface. The position and shape of the opening cuts may be predetermined by the control data, such that the opening cuts contribute to correction of the ametropia of the eye or do not counteract the correction of the ametropia of the eye.

The present method for generating control data may be further embodied such that further embodiments of the inventive method for generating cut surfaces in the cornea of an eye in order to correct ametropia can be carried out.

The cut surfaces may be generated in the cornea using the apparatus according to the present invention and the present method by pulsed laser radiation. Several processes may take place in the tissue within a time sequence. These processes may be initiated by pulsed laser radiation. If the power density of the radiation is above a threshold value during any pulse, an optical breakthrough may appear, which, for example, would form a plasma bubble in the cornea. The plasma bubble then grows, due to expanding gas after the optical breakthrough has formed. If the optical breakthrough is not maintained, the gas generated in the plasma bubble is absorbed by the surrounding tissue, and the bubble disappears. Tissue-separating effects, acting without plasma bubbles, are also possible. For the sake of simplicity, all such processes, including their effects, are summarized here by the term "optical breakthrough."

For tissue separation to occur, the laser radiation may be applied in pulsed form, with the pulse duration usually being below 1 ps. Thus, the power density required for the respective pulse to initiate the optical breakthrough is achieved within a narrow spatial area. High focusing of the laser beam in combination with the short pulses allows the optical breakthrough to be placed in the cornea with pinpoint accuracy. For cut surface generation, a series of optical breakthroughs is generated at the corresponding locations for the cut surface.

It will be appreciated that the features mentioned above and those yet to be explained below can be used not only in the indicated combinations, but also in other combinations or alone, without departing from the scope of the present invention.

BRIEF DESCRIPTION OF THE DRAWINGS

The invention will be explained in more detail below, by way of example and with reference to the enclosed drawings, which also disclose features essential to the invention and wherein.

DETAILED DESCRIPTION

Figure 1:
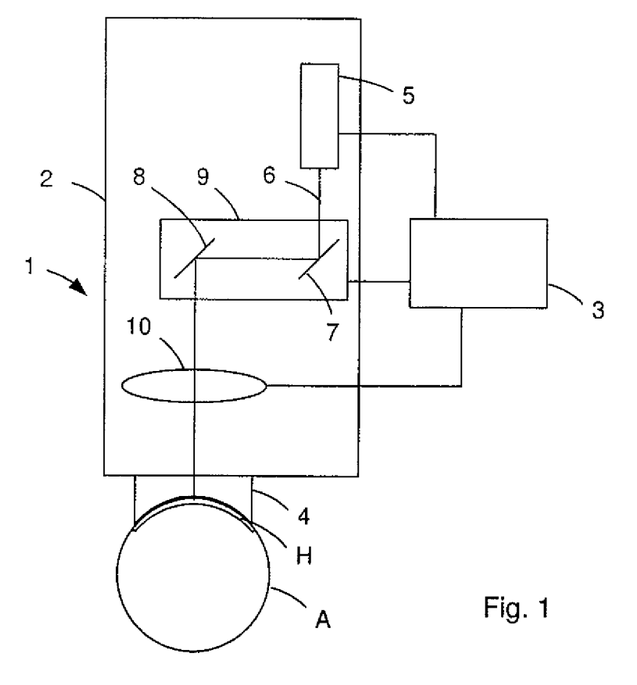
FIG. 1 shows a schematic view of an embodiment of the correcting device according to the invention.

In the embodiment shown in FIG. 1, the apparatus 1 for generating cut surfaces in the cornea H of an eye A in order to correct ametropia comprises a laser unit 2 and a control unit 3 for control of the laser unit 2. Further, the apparatus 1, which is also referred to hereinafter as a correcting apparatus, may comprise a contact element 4 which is detachably coupled with the laser unit 2 and with which the eye A to be corrected is in contact during operation of the apparatus 1.

As is evident from the schematic representation of FIG. 1, the laser unit 2 comprises a laser 5 emitting pulsed laser radiation 6. In this case, the pulse duration is, for example, in the femtosecond range (e.g. 50-800 fs) at a pulse repetition frequency of between 10 and 1 MHz.

The pulsed laser radiation 6 is focused through the contact element 4, by two deflecting mirrors 7, 8 forming a scanner 9 and by optics 10, into the cornea H of an eye A contacting the contact element 4 and is moved in the cornea H. This is effected under the control of the control unit 3, so that basically any locations in the cornea can have the pulsed laser radiation 6 applied thereon.

Of course, the scanner may also be designed in any other manner known to the person skilled in the art.

The control unit 3 may control the laser unit 2 such that an optical breakthrough for tissue separation is generated at the respective focus location in the cornea H. The focus locations are selected to be adjacent each other such that a desired cut surface can be generated in the cornea H. The focus locations may be adjacent each other such that the tissue is cut through completely between the focus locations. However, it is also possible that small tissue bridges remain, so that the cut surface can be referred to as a perforated cut surface.

The laser unit 2 and the control unit 3 are shown in a schematic and simplified manner in FIG. 1. Thus, for example, the optics 10, depicted as a lens, may comprise several optical elements, suitably arranged along the beam path from the laser 5 to the contact element 4.

The correction apparatus 1 may be operated such that, in order to correct ametropia (in this case, for example, correction of myopia and astigmatism), a preferably lens-shaped partial volume 11 (hereinafter also referred to as a lenticle) in the cornea H is separated from the surrounding corneal material by the pulsed laser radiation 6. This is preferably carried out such that first the rear surface 12 (FIG. 3) of the lenticle 11 and then the front surface 13 of the lenticle 11 is cut. In order to allow the lenticle 11, separated from the residual corneal material, to be removed from the cornea H, first and second opening cuts 14, 15, each extending from the lenticle 11 to the anterior corneal surface 16, are provided, as schematically shown in FIGS. 2 and 3.

The lenticle 11 can then be removed from the cornea H in a known manner through the first or second opening cut 14, 15. Due to the missing corneal volume (lenticle 11), the cornea will change its shape in this area. Prior to carrying out the method, the shape of the lenticle was selected such that the shape of the cornea after removal of the lenticle results in the desired correction of ametropia.

Figure 2:
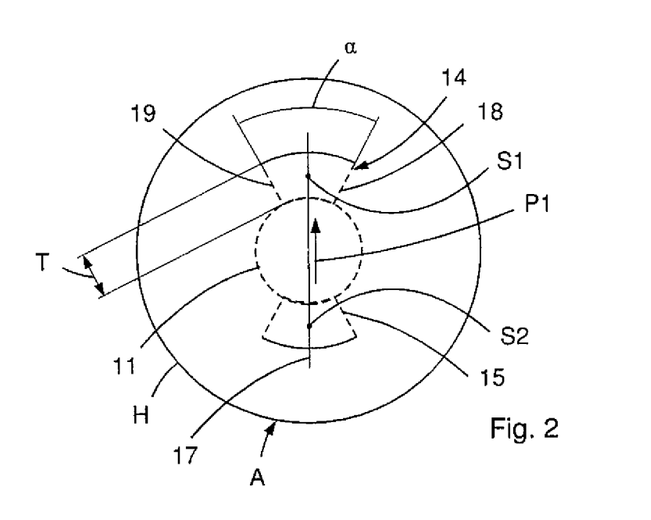
FIG. 2 shows a top view of an eye after carrying out the method according to the invention for generating cut surfaces in the cornea of an eye for correction of ametropia.
Figure 3:
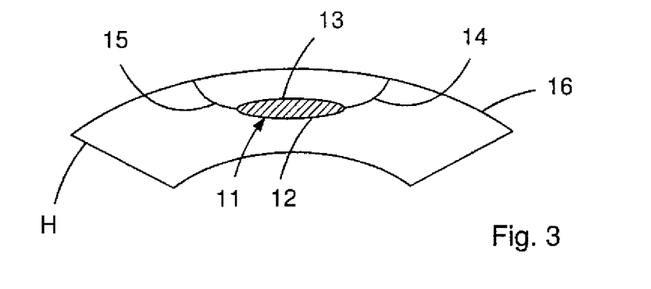
FIG. 3 shows a cross-sectional view of the cornea H along the line 17 of FIG. 2.

In the described exemplary embodiment of FIGS. 2 and 3, two opening cuts 14 and 15 have been performed and the shapes and positions of the opening cuts 14 and 15 are selected such that any still existing astigmatism of the eye A is also corrected thereby.

In other words, the invention takes into consideration the fact that even the very small opening cuts 14 and 15 may have an influence on the astigmatism of the eye A. This per se undesired effect is used in the invention to correct an existing astigmatism of the eye A.

In the described exemplary embodiment, it is assumed that the steepest axis of astigmatism in FIG. 2 extends from top to bottom as indicated by the arrow P1. In this case, the two opening cuts 14 and 15 are arranged such that their centers of area S1 and S2 are located on a straight line 17, which is parallel to or coincides with, the axis of astigmatism P1. Merely for the sake of clearer illustration, FIG. 2 shows the axis of astigmatism P1 slightly laterally of the straight line 17.

By this arrangement of the opening cuts 14 and 15, the astigmatism of the eye A is reduced due to the opening cuts 14 and 15.

As is evident from FIG. 2, the opening cuts 14 and 15, when viewed in the top view of FIG. 2, are respectively provided as circular ring segments. Since both opening cuts 14 and 15 are identical, only the first opening cut 14 will be described in more detail below.

The two straight sides 18 and 19 of the opening cut 14 have the same length T (FIG. 2), said length being between 0.1 and 1 mm or between 0.2 and 0.4 mm in the exemplary embodiment described here. Further, the two straight sides 18 and 19 enclose an angle α, which may range from 30°-120° or from 40°-80°.

Figure 4:
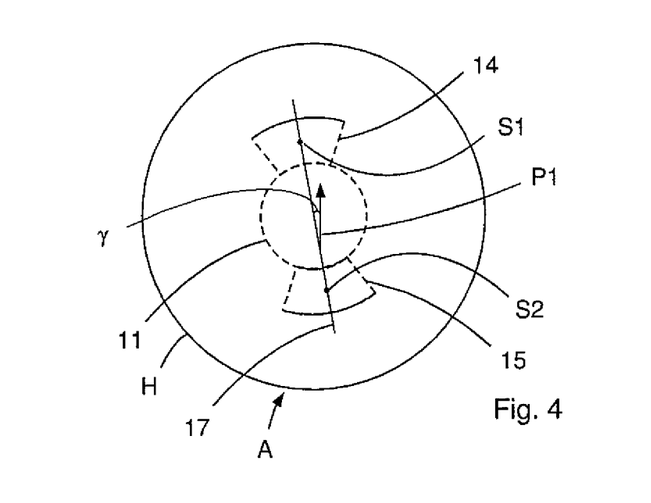
FIG. 4 shows a top view of an eye after carrying out the correcting method of the invention according to another embodiment.

FIG. 4 shows a modification of the embodiment of FIGS. 2 and 3. In this modification, the opening cuts 14 and 15 are placed such that the straight line 17 connecting the centers of area S1, S2 encloses an angle γ with the axis of astigmatism P1, said angle being 10° here. Even with this modification, an excellent correction of astigmatism is still achieved by the opening cuts 14 and 15.

Figure 5:
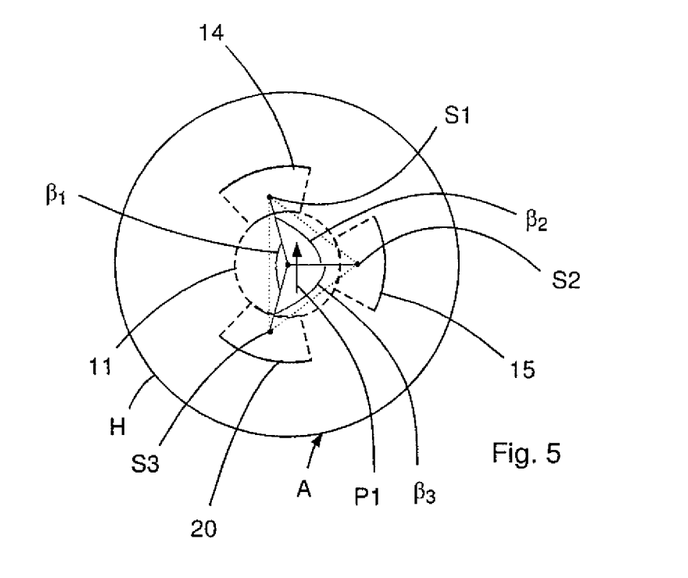
FIG. 5 shows a top view of an eye after carrying out the correcting method of the invention according to yet another embodiment.

As is evident from the embodiment shown in FIG. 5, three opening cuts 14, 15 and 20 have been carried out. The opening cuts 14, 15 and 20 are mutually spaced apart, with the centers of area S1, S2 and S3 defining a triangle, which is indicated by a dotted line in FIG. 5.

In order to achieve a correction of astigmatism by the opening cuts 14, 15 and 20, the opening cuts 14, 15 and 20 are located at unequal angular distances from one another on the circumference of the lenticle 11, as is evident from FIG. 5. Thus, the angle $\beta_1$ is 150° and the angles $\beta_2$ and $\beta_3$ are each 105°. Due to this asymmetrical angular distribution of the opening cuts 14, 15 and 20, the desired correction of astigmatism is achieved.

Figure 6:
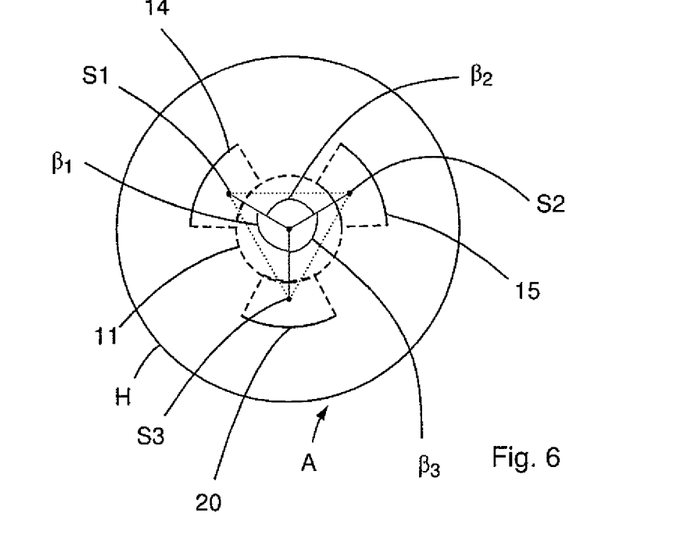
FIG. 6 shows a top view of an eye after carrying out the correcting method of the invention according to another embodiment.

However, it is also possible to distribute the opening cuts 14, 15 and 20 at equal angles, as shown in FIG. 6. In this case, the angles $\beta_1$, $\beta_2$ and $\beta_3$ are each 120°. This distribution of the opening cuts is selected if no correction of astigmatism by the opening cuts 14, 15 and 20 is desired. This may be the case, for example, if no astigmatism, but only a myopia has to be corrected. Thus, the opening cuts 14, 15 and 20 can be provided such that there is no influence on the astigmatism. As is evident from FIG. 6, the triangle defined by the centers of area S1, S2 and S3 is then an equilateral triangle.

Further, it is possible for the opening cuts 14, 15 and 20 in FIG. 6 to be arranged and shaped such that they contribute to the desired correction of myopia.

Figure 7:
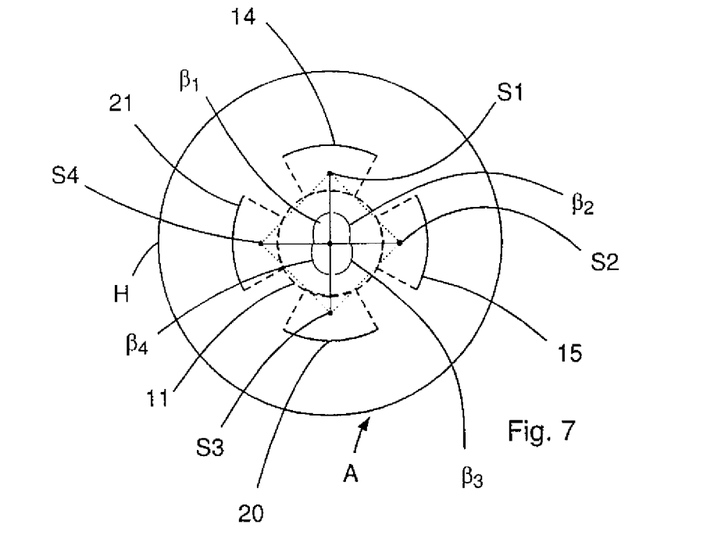
FIG. 7 shows a top view of an eye after carrying out the correcting method of the invention according to yet another embodiment.

Providing the opening cuts without influencing the astigmatism of the cornea H is also possible in the case of four opening cuts, as shown in FIG. 7. The four opening cuts 14, 15, 20 and 21 are again distributed at equal angles on the circumference of the lenticle 11 so that, in this case, the centers of area S1, S2, S3 and S4 define a square.

In general, it can be said that n opening cuts (with n>2) can be provided such that their centers of area form a regular n-sided polygon so as to cause no influence on astigmatism by the n opening cuts.

Figure 8:
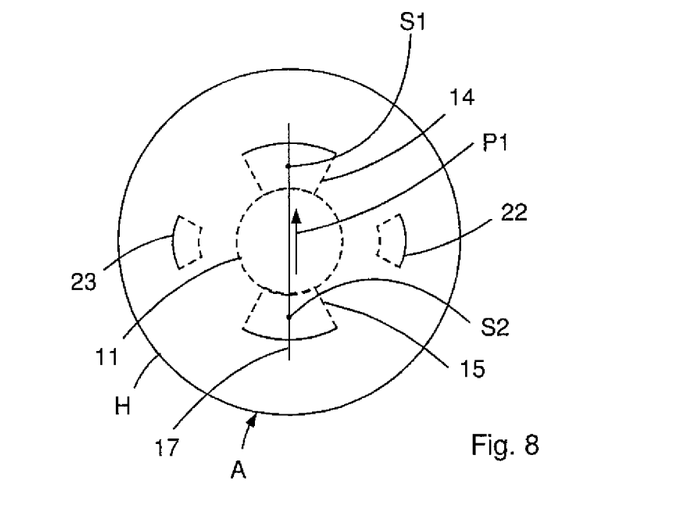
FIG. 8 shows a top view of an eye after carrying out the correcting method of the invention according to another embodiment.

As indicated in FIG. 8, which shows a further development of the embodiments of FIGS. 2 and 3, relieving cuts 22, 23 can be carried out in addition to the opening cuts 14, 15, said relieving cuts extending from the anterior surface of the cornea H into the latter, but not up to the lenticle 11. These relieving cuts 22, 23 can be used in order to correct the ametropia to be corrected by the lenticle 11 and/or of the astigmatism (arrow P1).

The invention claimed is:

1. A method for generating cut surfaces in a cornea of an eye in order to correct ametropia using an apparatus, said apparatus comprising:
a laser unit, which focuses pulsed laser radiation into the cornea and moves said focused radiation therein in order to generate cut surfaces within the cornea; and a control unit, which controls the laser unit for generating cut surfaces such that a predetermined lenticle to be removed is separated from the surrounding corneal material within the cornea by at least one cut surface, the method comprising:
forming at least two mutually spaced apart cut surfaces as opening cuts that are structured such that the lenticle or a portion thereof can be removed therethrough and that are structured such that the opening cuts do not lead to a corneal flap that can be folded back, each opening cut extending from the lenticle within the cornea to an anterior corneal, and
selecting a position and a shape of each opening cut such that the opening cuts contribute to the correction of the ametropia of the eye or do not counteract the correction of the ametropia of the eye being made.

2. The method as claimed in claim 1, wherein the position and shape of the opening cuts are selected such that the correction of the ametropia of the eye is counteracted such that the opening cuts do not generate additional astigmatism of the eye.

3. The method as claimed in claim 1, wherein the ametropia to be corrected comprises an astigmatism of the eye.

4. The method as claimed in claim 1, wherein the position and shape of the opening cuts are selected such that they correct higher-order errors of refracting power of the cornea.

5. The method as claimed in claim 1, wherein the control unit controls the laser unit such that at least three spaced apart opening cuts are generated such that the centers of area of the opening cuts coincide with the corners of a regular polygon.

6. The method as claimed in claim 1, wherein the control unit controls the laser unit such that the cut length of at least one opening cut from the anterior corneal surface to the lenticle differs from the cut lengths of the other opening cuts.

7. The method as claimed in claim 1, wherein the control unit controls the laser unit such that exactly two mutually spaced apart opening cuts are generated so that the centers of area of the opening cuts are located on a straight line which, when viewed in a top view of the eye, is parallel to an axis of astigmatism of the eye or intersects said axis at a maximum angle of 10° degree.

8. The method as claimed in claim 1, wherein the control unit controls the laser unit such that at least one of the opening cuts, when viewed in a top view of the eye, has a geometrical shape of a circular ring segment.

9. The method as claimed in claim 8, wherein the control unit controls the laser unit such that opposite straight sides of the circular ring segment enclose an angle of between 30° degree and 120° degree.

10. The method as claimed in claim 8, wherein the control unit controls the laser unit such that opposite straight sides of the circular ring segment enclose an angle of between 45° degree and 80° degree.

11. The method as claimed in claim 8, wherein the control unit controls the laser unit such that the opposite straight sides of the circular ring segment have a length of between 0.1 mm and 1 mm.

12. The method as claimed in claim 8, wherein the control unit controls the laser unit such that the opposite straight sides of the circular ring segment have a length of between 0.2 mm and 0.4 mm.

13. The method as claimed in claim 1, wherein the control unit controls the laser unit such that a further cut surface is provided as a relieving cut, which extends from the anterior corneal surface into the cornea, but not up to the lenticle, the location and shape of the relieving cut being selected such that said relieving cut contributes to the correction of the ametropia of the eye.

14. The method as claimed in claim 1, wherein the control unit controls the laser unit such that at least one of the cut surfaces is generated as a perforated cut surface.

15. A method for generating cut surfaces in the cornea of an eye in order to correct ametropia, comprising: focusing a pulsed laser radiation into the cornea for generating cut surfaces in the cornea at a focus; and moving said focus within in said cornea such that a predetermined lenticle to be removed is separated from the surrounding corneal material in the cornea by at least one cut surface, and such that at least two mutually spaced apart cut surfaces are provided as opening cuts that are structured such that the lenticle or a portion thereof can be removed therethrough and that are structured such that the opening cuts do not lead to a corneal flap that can be folded back, each opening cut extending from the lenticle to an anterior corneal surface of said cornea, wherein the position and shape of each of the opening cuts is selected such that the opening cuts contribute to the correction of the ametropia of the eye, or do not counteract the correction of the ametropia of the eye being made.

16. The method as claimed in claim 15, wherein the position and shape of the opening cuts are selected such that the correction of the ametropia of the eye is counteracted and so that the opening cuts do not generate additional astigmatism of the eye.

17. The method as claimed in claim 15, wherein the ametropia to be corrected comprises an astigmatism of the eye.

18. The method as claimed in claim 15, wherein a position and a shape of each of the opening cuts is selected such that the opening cuts correct higher-order errors of refracting power of the cornea.

19. The method as claimed in claim 15, wherein at least three mutually spaced apart opening cuts are generated such that their centers of area of said opening cuts coincide with corners of a regular polygon.

20. The method as claimed in claim 15, wherein a cut length of at least one opening cut from the anterior corneal surface to the lenticle differs from cut lengths of the other opening cuts.

21. The method as claimed in claim 15, wherein exactly two mutually spaced apart opening cuts are generated such that centers of area of the opening cuts are located on a straight line which, when viewed in a top view of the eye, is parallel to an axis of astigmatism of the eye or intersects said axis at a maximum angle of 10.degree.

22. The method as claimed in claim 15, wherein at least one of the opening cuts, when viewed in a top view of the eye, has a geometrical shape of a circular ring segment.

23. The method as claimed in claim 22, wherein the at least one opening cut is carried out such that opposite straight sides of the circular ring segment enclose an angle of between 30° degree and 120° degree.

24. The method as claimed in claim 22, wherein the at least one opening cut is carried out such that opposite straight sides of the circular rings enclose an angle between 45° degree and 80° degree.

25. The method as claimed in claim 22, wherein the at least one opening cut is carried out such that the opposite straight sides of the circular ring segment have a length of between 0.1 mm and 1 mm.

26. The method as claimed in claim 22, wherein the at least one opening cut is carried out such that the opposite straight sides of the circular ring segment have a length of between 0.2 mm and 0.4 mm.

27. The method as claimed in claim 15, wherein a further cut surface is provided as a relieving cut, extending from the anterior corneal surface into the cornea, but not up to the lenticle, the position and shape of the relieving cut being selected such that it contributes to the correction of the ametropia of the eye.

28. The method as claimed in claim 15, wherein at least one of the cut surfaces is generated as a perforated cut surface.

29. The method as claimed in claim 15, wherein the lenticle is removed from the cornea through one of the opening cuts.

* * * * *

UNITED STATES PATENT AND TRADEMARK OFFICE
CERTIFICATE OF CORRECTION

PATENT NO. : 8,956,344 B2
APPLICATION NO. : 12/109917
DATED : February 17, 2015
INVENTOR(S) : Christoph Russman et al.

Page 1 of 1

It is certified that error appears in the above-identified patent and that said Letters Patent is hereby corrected as shown below:

In the specification

Col. 3, line 2, delete "co-meal" and insert --corneal--

Col. 4, line 5, delete "cornmeal" and insert --corneal--

Signed and Sealed this
Sixteenth Day of February, 2016

Michelle K. Lee
*Director of the United States Patent and Trademark Office*